(12) United States Patent
Parsons

(10) Patent No.: US 11,587,229 B2
(45) Date of Patent: Feb. 21, 2023

(54) RETAINED SURGICAL ITEMS

(71) Applicant: Institute For Cancer Research, Philadelphia, PA (US)

(72) Inventor: Rosaleen B. Parsons, Philadelphia, PA (US)

(73) Assignee: Institute For Cancer Research, Philadelphia, PA (US)

(*) Notice: Subject to any disclaimer, the term of this patent is extended or adjusted under 35 U.S.C. 154(b) by 190 days.

(21) Appl. No.: 17/036,421

(22) Filed: Sep. 29, 2020

(65) Prior Publication Data

US 2021/0104038 A1 Apr. 8, 2021

Related U.S. Application Data

(60) Provisional application No. 62/911,415, filed on Oct. 7, 2019.

(51) Int. Cl.
| | | |
|---|---|---|
| G06T 7/00 | (2017.01) | |
| A61B 90/00 | (2016.01) | |
| G16H 30/20 | (2018.01) | |
| G06T 7/62 | (2017.01) | |
| G06T 7/13 | (2017.01) | |
| G06T 7/90 | (2017.01) | |
| G06T 7/136 | (2017.01) | |

(52) U.S. Cl.
CPC ............ *G06T 7/0012* (2013.01); *A61B 90/37* (2016.02); *G06T 7/13* (2017.01); *G06T 7/136* (2017.01); *G06T 7/62* (2017.01); *G06T 7/90* (2017.01); *G16H 30/20* (2018.01); *G06T 2207/10116* (2013.01); *G06T 2207/30004* (2013.01)

(58) Field of Classification Search
CPC ......... G06T 7/0012; G06T 7/136; G06T 7/62; G06T 7/13; G06T 7/90; G06T 2207/30004; G06T 2207/10116; A61B 90/37; G16H 30/20
See application file for complete search history.

(56) References Cited

U.S. PATENT DOCUMENTS

| | | |
|---|---|---|
| 7,180,014 B2 * | 2/2007 | Farber .................... G16H 40/20 606/1 |
| 7,557,710 B2 | 7/2009 | Sanchez et al. |
| 7,774,244 B2 | 8/2010 | Kreiner et al. |
| 9,168,104 B2 | 10/2015 | Dein |

(Continued)

FOREIGN PATENT DOCUMENTS

WO WO-2013082289 A1 * 6/2013 ............. A61B 5/055

OTHER PUBLICATIONS

Kumar et al., "Imaging of retained surgical items: A pictorial review including new innovations", Indian Journal of Radiology and Imaging, 2017, 27, pp. 354-361.

*Primary Examiner* — Shefali D Goradia
(74) *Attorney, Agent, or Firm* — Armstrong Teasdale LLP

(57) ABSTRACT

The present disclosure is directed, in part, to methods and systems of intra-operatively identifying a retained surgical item by imaging a surgical item with an intra-operative imaging device to obtain image data, imaging a patient suspected of having a retained surgical item with an intra-operative imaging device to obtain image data, interacting the image data to a module configured to identify the surgical item from the intra-operative surgical item image data, and identifying the retained surgical item from the surgical item image data.

18 Claims, 2 Drawing Sheets

(56) References Cited

U.S. PATENT DOCUMENTS

| | | | |
|---|---|---|---|
| 9,317,920 B2 * | 4/2016 | Gluncic | .................. A61B 5/055 |
| 9,675,273 B2 * | 6/2017 | Gluncic | ................ G06T 7/0012 |
| 9,792,682 B2 | 10/2017 | Gluncic et al. | |
| 2017/0143284 A1 | 5/2017 | Sehnert et al. | |
| 2020/0273581 A1 * | 8/2020 | Wolf | ...................... G16H 70/20 |

* cited by examiner

RETAINED SURGICAL ITEMS

FIELD

The present disclosure is directed, in part, to methods and systems of intra-operatively radiographically identifying or excluding a retained surgical item in a patient suspected of having a retained surgical item.

BACKGROUND

A retained surgical item (RSI) is any item that is inadvertently left in a patient's body in an operative setting. According to the National Quality Forum (NQF), 2000-4000 RSI cases occur each year in the United States. Rates are highest in emergency cases, patients with morbid obesity, and rural and teaching hospitals. Although the most common retained items in the past were sponges, with the rapid emergence of minimally invasive surgeries smaller broken parts, such as clips, are being retained. The estimated cost to remove an RSI is over $63,000 per hospital stay and malpractice claims can reach millions of dollars. Hospitals have developed policies and recommendations to reduce the incidence of RSI. A common policy is to obtain a portable film of the operative site to try and identify the RSI. The ability to detect the RSI using plain radiography has been reported in several published studies to be poor (i.e., 33-50%). This poor detection rate is not surprising because the images are obtained using portable techniques, in a single plane with an open surgical field. Typically, there are numerous expected clips, sponges, hemostats, etc., overlying the surgical field which can make it difficult to localize an unexpected item. The second issue, which is correctable and contributes to the poor detection, is lack of a reference catalog of x-ray images which include the sizes of the instruments. The interpreting radiologist often struggles trying to rapidly identify a "clip house," for example, when the radiologist may have no information regarding what a clip house looks like outside the patient. The incidence of retained items is ongoing and is a major health concern that impacts every operating room in the world.

Future recommendations would be to develop methods and systems employing a central processing imaging facility that would digitally store images and measurements of all operating room (OR) items. There are thousands of items that are used in the OR and are often unique per specialty. Therefore, a list of commonly used items could be customized to the facility.

SUMMARY

The present disclosure provides methods of imaging a patient during or after surgery in a surgical suite, wherein the patient is suspected of having a retained surgical item (RSI), the methods comprising the steps of: determining whether the patient contains the RSI by: obtaining or having obtained an image, such as a digital radiograph, of the patient or a portion of the patient suspected of containing the RSI; and comparing the image of the patient or portion of the patient to one or more images of surgical items, which may be stored in a digital archive; and if the image of the patient depicts the image of one or more images of surgical items, then treating the patient by removing the RSI; and if the image of the patient does not depict the image of one or more images of surgical items, then continuing the surgical procedure on the patient; wherein the one or more images of surgical items is stored in a computer database and contains at least one image of each surgical item present in the surgical suite.

The present disclosure also provides systems for intra-operatively identifying a suspected retained surgical item in a patient, the systems comprising: an imaging device, such as a portable digital x-ray machine, for obtaining intra-operative surgical image data of the patient; and a module comprising a processor and a database; wherein the database comprises surgical item image data for a plurality of surgical items, each surgical item image data comprising one or more of a shape, a size, or an outline of the surgical item; and wherein the module is configured for a user to identify a retained surgical item from the surgical item image data present in the intra-operative surgical image data of the patient by comparing the intra-operative surgical image data of the patient to the surgical item image data in the database.

The present disclosure also provides methods of identifying a retained surgical item in a patient in an operating suite, the methods comprising: imaging the patient, or a portion of the patient suspected of containing the retained surgical item, with an imaging device, such as a portable digital x-ray machine, to produce intra-operative surgical image data of the patient; interacting with a module comprising a processor and a database, wherein the database comprises surgical item image data for a plurality of surgical items within the operating suite, wherein each surgical item image data comprises one or more of a shape, a size, or an outline of the surgical item; and identifying the retained surgical item from the surgical item image data present in the intra-operative surgical image data of the patient by comparing the intra-operative surgical image data of the patient to the surgical item image data in the database.

The present disclosure also provides any one or more of the methods of imaging a patient during or after surgery in a surgical suite, wherein the patient is suspected of having an RSI, methods of identifying an RSI in a patient in an operating suite or systems for intra-operatively identifying a suspected RSI in a patient, substantially as described with reference to the accompanying examples and/or figures.

DESCRIPTION OF EMBODIMENTS

Unless defined otherwise, all technical and scientific terms have the same meaning as is commonly understood by one of ordinary skill in the art to which the disclosed embodiments belong.

As used herein, the terms "a" or "an" mean "at least one" or "one or more" unless the context clearly indicates otherwise.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive and open-ended and include the options following the terms, and do not exclude additional, unrecited elements or method steps.

As used herein, the terms "individual," "subject," and "patient," used interchangeably, mean any animal, including humans.

It should be appreciated that particular features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

The present disclosure provides methods of imaging a patient during or after surgery in a surgical suite, wherein the patient is suspected of having an RSI, the methods comprising the steps of: a) determining whether the patient contains the RSI by: i) obtaining or having obtained an image of the patient or a portion of the patient suspected of containing the RSI; and ii) comparing the image of the patient or portion of the patient to one or more images of surgical items; and if the image of the patient depicts the image of one or more images of surgical items, then treating the patient by removing the RSI; and if the image of the patient does not depict the image of one or more images of surgical items, then continuing the surgical procedure on the patient; wherein the one or more images of surgical items is stored in a computer database and contains at least one image of each surgical item present in the surgical suite.

In some embodiments, the surgical item is present in a semi-restricted surgical suite, a restricted surgical suite, or both. The surgical suite may be a general surgical suite, an orthopedic suite, a neurological suite, a urological surgical suite, or a cardiac/thoracic suite.

Figure 2:
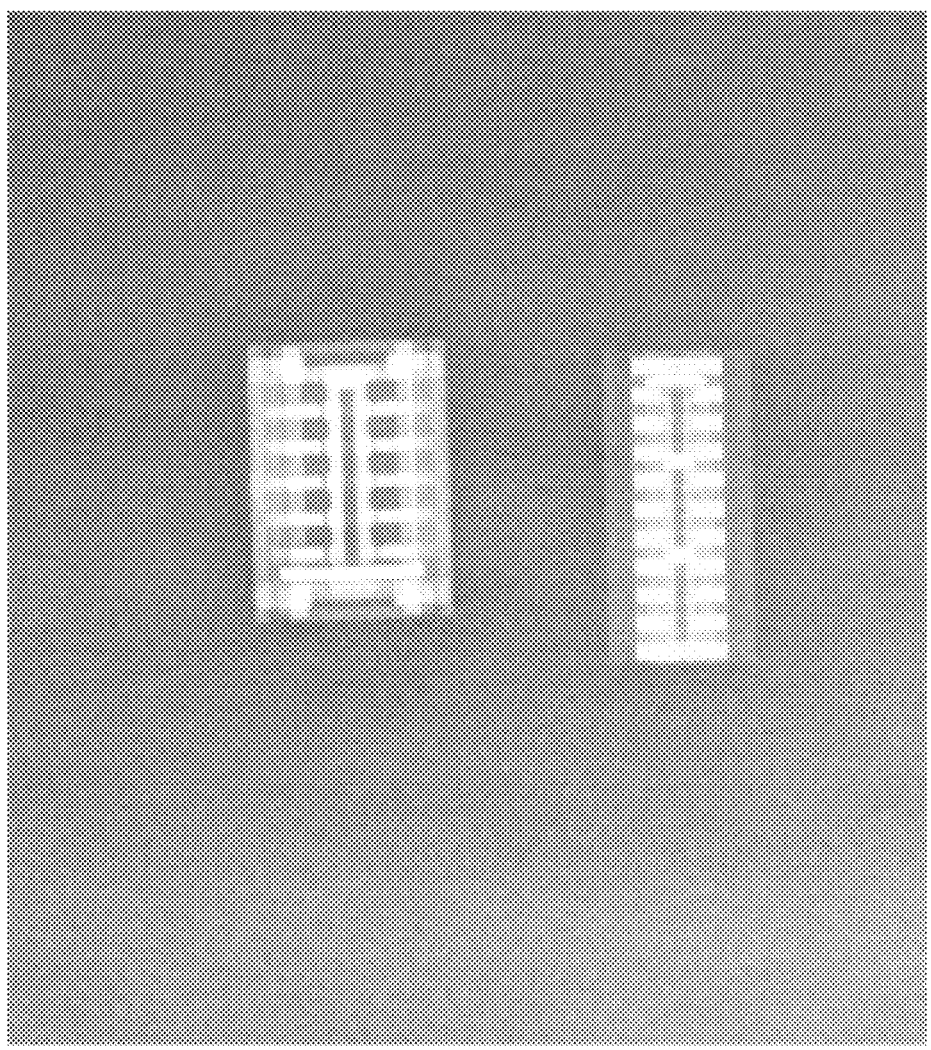
FIG. 2 shows a representative digital X-ray of a clip house stored in a digital library of surgical items.

In some embodiments, surgical items (which may be RSIs) include, but are not limited to, a needle, a knife blade, a safety pin, a scalpel, a clamp, a scissors, a sponge, a towel, an electrosurgical adapter, a tweezers, a forcep, a suction tip, and/or a suction tube. In some embodiments, the surgical item is a broken portion of a surgical item. A representative digital x-ray of a clip house is shown in FIG. 2.

Figure 1:
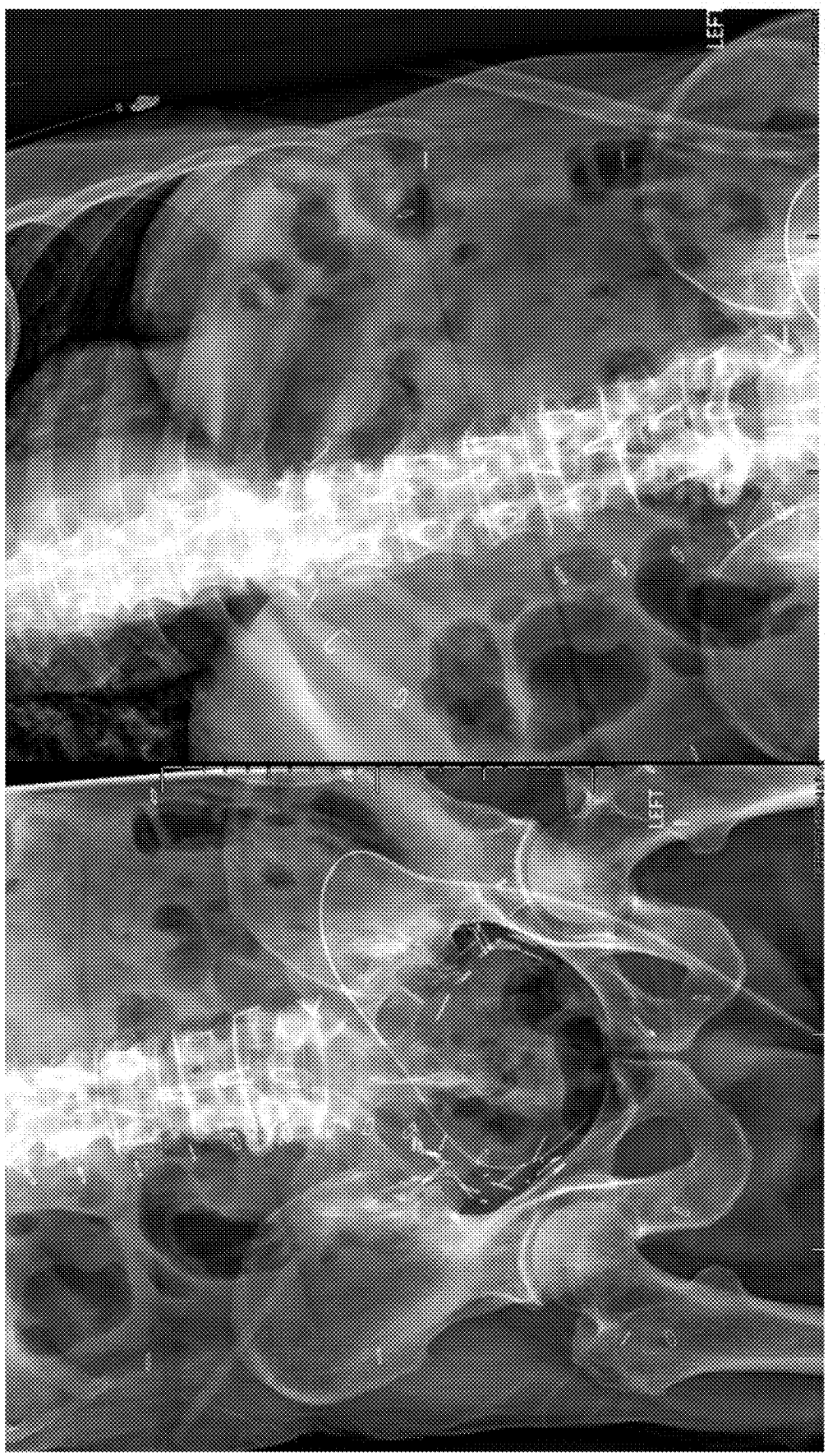
FIG. 1 shows a representative digital X-ray of the pelvic region of a human.

In some embodiments, both the image of the patient, or a portion of the patient suspected of containing the RSI, and the one or more images of surgical items is a digital X-ray. A representative digital x-ray of a pelvic region of a human is shown in FIG. 1. In some embodiments, the one or more images of surgical items comprises a plurality of images of commonly used surgical items present in a surgical suite. In some embodiments, the plurality of images may be stored in a picture archiving and communications system (PACS). The plurality of images of each surgical item present in the surgical suite may also comprise images of each surgical item present in the surgical suite at different angles and/or views. In some embodiments, the plurality of images of each surgical item present in the surgical suite represents the actual dimensions (i.e., size) of the surgical item present in the surgical suite.

In some embodiments, the image of the patient, or portion of the patient suspected of containing the RSI, is obtained during surgery. In some embodiments, the image of the patient, or portion of the patient suspected of containing the RSI, is obtained after completion of the surgery, but before the patient is completely closed.

The present disclosure also provides systems for intra-operatively identifying a suspected retained surgical item in a patient, the systems comprising: a) an imaging device, such as a digital x-ray machine, for obtaining intra-operative surgical image data of the patient and b) a module comprising a processor and a database: wherein the database comprises surgical item image data for a plurality of surgical items, each surgical item image data comprising one or more of a shape, a size, or an outline of the surgical item; and wherein the module is configured for a user to identify a retained surgical item from the surgical item image data present in the intra-operative surgical image data of the patient by comparing the intra-operative surgical image data of the patient to the surgical item image data in the database.

In some embodiments, the imaging device, such as a portable x-ray machine, is positioned to image a portion of the patient suspected of containing the retained surgical item. The image data, such as a digital radiograph, may be data for one or more still images. Any intra-operative imaging device configured to obtain such data may be employed. Non-limiting examples of such systems include digital portable x-ray machines, such as those produced by manufacturers such as Siemens, Philips, and GE. Such devices would be able to link electronically to a digital archive of surgical items, such as PACS. In some embodiments, the surgical item image data and/or the intra-operative surgical image data of the patient comprises digital X-ray data.

In some embodiments, the digital radiographic imaging device is configured to obtain the surgical item image data before, during, and after a surgical procedure. In some embodiments, the surgical procedure is an operation, including an open surgical procedure, or a minimally-invasive surgical procedure, including endoscopic procedures, such that there is at least one opening into a body where a surgical item could be left inside of a body. A surgical procedure can include the actual procedure itself, as well as the period of time during preparation before and after the conclusion of the surgical procedure (e.g., performing initial or final counting and identification of a surgical sharp object, etc.).

In some embodiments, the module further comprises automated shape recognition. This surgical item automated shape recognition module is a functional module that is configured to identify a surgical item from intra-operative surgical item image data obtained by the intra-operative imaging device, e.g., as described above. The term "module" refers to a combination of hardware and/or software which is configured to perform a specific given function or functions. In some embodiments, the images are sent digitally. In some embodiments, a given module may be a programmable digital microprocessor such as available in the form of an electronic controller, mainframe, server or personal computer (desktop or portable). Where the module is programmable, suitable programming can be communicated from a remote location to the module, or previously saved in a computer program product (such as a portable or fixed computer readable storage medium, whether magnetic, optical or solid-state device based). For example, a magnetic medium or optical disk may carry the programming and can be read by a suitable reader communicating with a given module at its corresponding station. It should be understood that the terms "automated shape recognition", "automated shape identification", and "machine vision", can all be used to indicate the automatic identification of surgical items (such as needles, knife blades, safety pins, scalpels, clamps, scissors, sponges, towels, electrosurgical adapters, tweezers, forceps, suction tips and tubes, scopes, ultrasound tissue disruptors, asepto bulbs, cryotomes and cutting laser guides, and measuring devices) from one or more types of image data obtained for the object, e.g., one or more types of image data relating to the size, shape, aspect ratio, outline, color, or other imageable parameter of the surgical item.

Surgical item automated shape recognition modules are modules that are configured to identify a surgical item without the need for an identifying label by a method of automated shape recognition, such as machine vision. Automated shape recognition is a process by which the identification of surgical item is performed using one or more of the size, shape, aspect ratio, outline, color, or other distinctive feature present in the image data of the surgical item. Automated shape recognition can be performed in two-dimensions or three-dimensions. For example, a digital camera (either gray-scale or color vision camera) can obtain image data of a surgical item, which image data can then be processed by the automated shape recognition module (and specifically by software and/or hardware of the module) using a machine vision and image processing technique. In some embodiments, with the use of artificial intelligence, three-dimensional models could be used at the time of reviewing the images.

Any machine vision and image processing technique may be employed. To distinguish between specific surgical items, the module may use variables such as the size, shape, aspect ratio, outline, or color of the of the surgical item, certain angles or curves, the two-dimensional projection that is unique to a given surgical item, etc. For example, the shape formed by a certain size of surgical item can be used to identify the surgical item via automated shape recognition protocols.

The software can take several steps to process an image. The image may first be manipulated to reduce noise or to convert many shades of gray to a simple combination of black and white (binarization). Following the initial simplification, the software may count and/or identify objects in the image. Any suitable software program can be used, including commercially available software programs, as disclosed above, are available and can be used in any of the embodiments described herein. The systems can include use of a software program to process images and detect relevant features for identifying a surgical item.

A given automated shape recognition module may employ pre-existing surgical item data in a given automated shape recognition protocol, e.g., a reference with which to compare the obtained image data to identify a given surgical item. This pre-existing surgical item data may be provided in the shape recognition module using a variety of different protocols and may be stored digitally in a PACS. For example, the pre-existing surgical item data may be introduced into the shape recognition module at the time of manufacture, where the data may or may not be updatable depending on the nature of the particular module. Alternately, prior to the beginning of a given surgical procedure, the data about the specific surgical item (and other items as desired) which are to be identified using automated shape recognition (i.e., machine vision) are programmed into the software.

In some embodiments, the module is configured to identify the suspected retained surgical item from the surgical item image data in the database within the intra-operative surgical image data of the patient by analysis comprising pixel counting, thresholding, segmentation, pattern recognition, detection of an angle or curve, measurement of an area or size, determination of an aspect ratio, edge detection, outline or silhouette detection, color recognition, or template matching, or any combination thereof. The analysis may incorporate machine vision software programs that can be used for automated shape identification through a number of different image processing techniques for identification of an object, such as pixel counting (counts the number of light or dark pixels), thresholding (converts an image with gray tones to simply black and white), segmentation (used to locate and/or count parts), pattern recognition (location of an object that may be rotated, partially hidden by another object, or varying in size), detection of particular angle or curve, measurement of area or size of an object, determining the aspect ratio of the object, edge detection, the outline or silhouette detection, the two- or three-dimensional projection of an object, template matching, color, etc. Examples of machine vision software programs that can be used with the subject invention include, but are not limited to, Insight-Explorer™ Vision software, IVC Studio™ software, National Instrument™ Vision Builder™ software, any suitable software programs sold by Dalsa™, Visionx™, Matrox™ Imaging, etc., or any other suitable machine vision software program. Also, in some embodiments, "template matching" of the outline or silhouette of a surgical item is used by a given shape recognition module to distinguish one surgical item from another.

In some embodiments, the analysis can use a combination of processing techniques to identify an object; for example, the detection of a particular shape and the measured size may be used to identify a particular surgical item. As such, more than one identification technique can be used to improve the accuracy and reliability of the identification process.

The term "system" can include the hardware means, software means, and data storage means used to analyze the information of the present invention. Systems may include a central processing unit (CPU), input means, output means, and data storage means, etc. Any computer-based system may be employed in any of the embodiments described herein.

The present invention also provides methods of identifying a retained surgical item in a patient in an operating suite, the methods comprising: a) imaging the patient, or a portion of the patient suspected of containing the retained surgical item, with an imaging device to produce intra-operative surgical image data of the patient; b) interacting with a module comprising a processor and a database, wherein the database comprises surgical item image data for a plurality of surgical items within the operating suite, wherein each surgical item image data comprises one or more of a shape, a size, or an outline of the surgical item; and c) identifying the retained surgical item from the surgical item image data present in the intra-operative surgical image data of the patient by comparing the intra-operative surgical image data of the patient to the surgical item image data in the database.

The surgical item can be present in any of the surgical suites described herein. The surgical item can be any of the surgical items described herein. In some embodiments, the database is a PACS. In some embodiments, the surgical item image data and/or the intra-operative surgical image data of the patient comprises digital X-ray data. In some embodiments, the imaging device is configured to obtain the surgical item image data before, during, and after a surgical procedure. The surgical procedure can be any of the surgical procedures described herein. The imaging device can be any of the imaging devices described herein. In some embodiments, the module may further comprise automated shape recognition, as described herein. The surgical item automated shape recognition modules can be any of those described herein.

The methods and systems described herein can be used with any surgical or other invasive procedure including, but not limited to, procedures conducted in an operating room, or outpatient surgery center, or any procedure where correct counts of surgical items is desired. Surgical item identification can be performed before surgery begins, after surgery has concluded, or at any time during the procedure. Identification can also be performed before any type of hollow organ closure (e.g., closure of an intestinal loop, cardiac chamber, peritoneum, etc.) or before wound or skin closure, etc.

The nature of the current system utilizes highly accurate methods of imaging, identifying, and when appropriate, treating patients suspected of having a retained surgical item. Safety is greatly enhanced for the patient by reducing the potential for an unnecessary re-exploration of the body cavity. In addition, safety is enhanced for all patients, because the time spent in the operating room counting and recounting surgical items is reduced, thereby reducing operating time for all procedures. The current system also decreases the likelihood of complications from a retained surgical foreign body, because the incidence of retained surgical foreign bodies is reduced. The enhanced medical record and medico-legal record of the surgical items counted are a further benefit as the responsibility of the decision makers is automated and accepted in real time as the decisions are made. The overall result is a safer operation for the patient and for the operating room personnel and less medico-legal exposure for the institution.

The current system also fits well with currently accepted protocols, which leads to ease of use and acceptance of the system by operating room personnel. Additionally, using the current system, no particular placement or arrangement of instruments on the surgical table is needed, in contrast to methods which use mechanical tray counting systems or other sensing modalities dependent upon a particular spatial arrangement. The current system permits the surgical personnel to place the items as desired, according to current protocol in all operating rooms. The ability to place instruments, etc., in their accustomed positions is advantageous because the arrangement of surgical implements in most operating rooms is determined by the personal preference of the scrub nurse. Using the current methods, the scrub nurse or technician is not required to re-train or follow a particular protocol, which could affect the surgeon's call for particular items. The current methods enhance the safety and speed of the operation as the scrub personnel are not preoccupied with manual counting while still carrying on the physical actions of the operation, which present day counting processes require.

In order that the subject matter disclosed herein may be more efficiently understood, examples are provided below. It should be understood that these examples are for illustrative purposes only and are not to be construed as limiting the claimed subject matter in any manner.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of imaging a patient during or after surgery in a surgical suite, wherein the patient is suspected of having a retained surgical item (RSI), the method comprising the steps of:
    determining whether the patient contains the RSI by:
        obtaining or having obtained an image of the patient or a portion of the patient suspected of containing the RSI; and
        comparing the image of the patient or portion of the patient to one or more images of surgical items; and
    if the image of the patient depicts the image of one or more images of surgical items, then treating the patient by removing the RSI; and
    if the image of the patient does not depict the image of one or more images of surgical items, then continuing the surgical procedure on the patient;
    wherein the one or more images of surgical items is stored in a computer database and contains at least one image of each surgical item present in the surgical suite; and
    wherein the surgical item is stored in a semi-restricted surgical suite or a restricted surgical suite.

2. The method according to claim 1, wherein the surgical item is a broken portion of a surgical item.

3. The method according to claim 1, wherein both the image of the patient, or a portion of the patient suspected of containing the RSI, and the one or more images of surgical items is a digital radiograph (X-ray).

4. The method according to claim 1, wherein the one or more images of surgical items comprises a plurality of images of commonly used surgical items present in the surgical suite.

5. The method according to claim 4, wherein the plurality of images of each surgical item present in the surgical suite comprises images of each surgical item present in the surgical suite at different angles and/or views.

6. The method according to claim 4, wherein the plurality of images of each surgical item present in the surgical suite represents the actual dimensions of the surgical item present in the surgical suite.

7. The method according to claim 1, wherein the computer database is a picture archiving and communications system (PACS).

8. A system for intra-operatively identifying a suspected retained surgical item in a patient, the system comprising:
    an imaging device for obtaining intra-operative surgical image data of the patient; and
    a module comprising a processor and a database;
        wherein the database comprises surgical item image data for a plurality of surgical items, each surgical item image data comprising one or more of a shape, a size, or an outline of the surgical item; and
        wherein the module is configured fix a user to identify a retained surgical item from the surgical item image data present in the intra-operative surgical image data of the patient by comparing the intra-operative surgical image data of the patient to the surgical item image data in the database;
        wherein the surgical item is stored in a semi-restricted surgical suite or a restricted surgical suite.

9. The system according to claim 8, wherein the imaging device is positioned to image a portion of the patient suspected of containing the retained surgical item.

10. The system according to claim 8, wherein the surgical item image data and/or the intra-operative surgical image data of the patient comprises digital X-ray data.

11. The system according to claim 8, wherein the imaging device is configured to obtain the surgical item image data before, during, and after a surgical procedure.

12. The system according to claim 8, wherein the module is configured to identify the suspected retained surgical item from the surgical item image data in the database within the intra-operative surgical image data of the patient by analysis comprising pixel counting, thresholding, segmentation, pattern recognition, detection of an angle or curve, measurement of an area or size, determination of an aspect ratio, edge detection, outline or silhouette detection, color recognition, or template matching, or any combination thereof.

13. The system according to claim 8, wherein the database is a picture archiving and communications system (PACS).

14. A method of identifying a retained surgical item in a patient in an operating suite, the method comprising:
   imaging the patient, or a portion of the patient suspected of containing the retained surgical item, with an imaging device to produce intra-operative surgical image data of the patient;
   interacting with a module comprising a processor and a database, wherein the database comprises surgical item image data for a plurality of surgical items within the operating suite, Wherein each surgical item image data comprises one or more of a shape, a size, or an outline of the surgical item; and
   identifying the retained surgical item from the surgical item image data present in the intra-operative surgical image data of the patient by comparing the intra-operative surgical image data of the patient to the surgical item image data in the database;
   wherein the surgical item is stored in a semi-restricted surgical suite or a restricted surgical suite.

15. The method according to claim 14, wherein the surgical item image data and/or the intra-operative surgical image data of the patient comprises digital X-ray data.

16. The method according to claim 14, wherein the imaging device is configured to obtain the surgical item image data before, during, and after a surgical procedure.

17. The method according to claim 14, wherein the module is configured to identify the suspected retained surgical item from the surgical item image data in the database within the intra-operative surgical image data of the patient by analysis comprising pixel counting, thresholding, segmentation, pattern recognition, detection of an angle or curve, measurement of an area or size, determination of an aspect ratio, edge detection, outline or silhouette detection, color recognition, or template matching, or any combination thereof.

18. The method according to claim 14, wherein the database is a picture archiving and communications system (PACS).

* * * * *

UNITED STATES PATENT AND TRADEMARK OFFICE
CERTIFICATE OF CORRECTION

PATENT NO. : 11,587,229 B2
APPLICATION NO. : 17/036421
DATED : February 21, 2023
INVENTOR(S) : Rosaleen B. Parsons It is certified that error appears in the above-identified patent and that said Letters Patent is hereby corrected as shown below:

In the Claims

Column 8, Claim 8, Line 47, delete the word "fix" and insert therefore -- for --.

Signed and Sealed this
Ninth Day of May, 2023

Katherine Kelly Vidal
*Director of the United States Patent and Trademark Office*